United States Patent
Stepp

(10) Patent No.: US 10,196,408 B2
(45) Date of Patent: Feb. 5, 2019

(54) PROCESS FOR PREPARING SILOXANOLS FROM METAL SALTS OF SILANOLS

(71) Applicant: Wacker Chemie AG, Munich (DE)

(72) Inventor: Michael Stepp, Ueberackern (AT)

(73) Assignee: WACKER CHEMIE AG, Munich (DE)

( * ) Notice: Subject to any disclaimer, the term of this patent is extended or adjusted under 35 U.S.C. 154(b) by 0 days.

(21) Appl. No.: 15/545,810

(22) PCT Filed: Nov. 15, 2016

(86) PCT No.: PCT/EP2016/077698
§ 371 (c)(1),
(2) Date: Jul. 24, 2017

(87) PCT Pub. No.: WO2017/097550
PCT Pub. Date: Jun. 15, 2017

(65) Prior Publication Data
US 2018/0016286 A1 Jan. 18, 2018

(30) Foreign Application Priority Data
Dec. 9, 2015 (DE) .................. 10 2015 224 732

(51) Int. Cl.
*C07F 7/18* (2006.01)
*C08G 77/06* (2006.01)
*C08G 77/16* (2006.01)
*C08G 77/24* (2006.01)

(52) U.S. Cl.
CPC ............ *C07F 7/188* (2013.01); *C07F 7/1804* (2013.01); *C08G 77/06* (2013.01); *C08G 77/16* (2013.01); *C08G 77/24* (2013.01)

(58) Field of Classification Search
None
See application file for complete search history.

(56) References Cited

U.S. PATENT DOCUMENTS

| 2,567,110 | A | 9/1951 | Hyde |
| 5,391,546 | A | 2/1995 | Le Ribault |
| 6,150,488 | A | 11/2000 | Martin |
| 2013/0145966 | A1 | 6/2013 | Schildbach et al. |
| 2014/0069301 | A1 | 3/2014 | Stepp et al. |
| 2014/0296556 | A1 | 10/2014 | Stepp et al. |
| 2015/0284413 | A1 | 10/2015 | Stepp et al. |
| 2017/0137445 | A1 | 5/2017 | Stepp et al. |

FOREIGN PATENT DOCUMENTS

| EP | 0 228 978 A1 | 7/1987 |
| WO | 00/40640 A1 | 7/2000 |
| WO | 2012/022544 A1 | 2/2012 |
| WO | 2012/159874 A1 | 11/2012 |
| WO | 2013075969 A1 | 5/2013 |
| WO | 2013174689 A1 | 11/2013 |
| WO | 2015140075 A1 | 9/2015 |
| WO | 15176977 A1 | 11/2015 |

OTHER PUBLICATIONS

Shchegolikhina, O.I. et al., Russian Chemical Bulletin, International Edition, vol. 56, No. 1, pp. 83-90, Jan. 2007: "cis_Tetra[(organo)(trimethylsiloxy)]cyclotetrasiloxanes: synthesis and mesomorphic properties".

*Primary Examiner* — Clinton A Brooks
(74) *Attorney, Agent, or Firm* — Brooks Kushman P.C.

(57) ABSTRACT

Siloxanes which are liquid at 25° C. and 1 bar, have 2% to 12% by weight of silanol groups and are of the formula (1):

$$M_a D_b T_c Q_d M'_e D'_f T'_g \qquad (1),$$

are prepared by reacting metal salts of silanols of the formula (2):

$$R_1 Si(OH)_{4-l-m}(O^- Z^{r+}_{/r})_m \qquad (2)$$

or condensation products thereof with silanes of the formula (3):

$$R'_n SiX_{4-n} \qquad (3)$$

in a ratio which is calculated by:

mol of organosiliconate of the general formula (2):
mol of silane of the general formula (3)=$x*(4-n)/m$, where x=0.8 to 1.2.

10 Claims, No Drawings

PROCESS FOR PREPARING SILOXANOLS FROM METAL SALTS OF SILANOLS

CROSS REFERENCE TO RELATED APPLICATIONS

This application is the U.S. National Phase of PCT Appln. No. PCT/EP2016/077698 filed Nov. 15, 2016, which claims priority to German Application No. 10 2015 224 732.5 filed Dec. 9, 2015, the disclosures of which are incorporated in their entirety by reference herein.

BACKGROUND OF THE INVENTION

1. Field of the Invention

The invention relates to liquid branched siloxanes having a high proportion of SiOH groups and to a process for preparation thereof.

2. Description of the Related Art

Branched siloxanes are typically prepared by hydrolysis/co-condensation of silanes having at least three hydrolysable radicals and optionally further mono-, di- or tetrafunctional silanes. According to the choice of starting compounds, the stoichiometry thereof, and the (co-)hydrolysis conditions, these compounds, which are typically referred to as silicone resins, are thus available in a wide variety. They serve as plasticizers, crosslinkers, etc. in a multitude of applications.

A great disadvantage of the siloxanes prepared by this route is that some hydrolysable radicals (usually alkoxy or chlorine radicals) remain in the product, which restrict storage stability and which can be released in an unwanted manner in the course of use. This is also one of the reasons why SiOH-rich branched siloxanes obtainable, for example, via use of this general process with high excesses of water, are unstable or condense to form high molecular weight structures and hence usually form solids: they can condense with residual hydrolysable groups to form structures of higher molecular weight. This unwanted condensation is also promoted by the typically non-neutral hydrolysis conditions during the (co-)hydrolysis, such that low molecular weight SiOH-rich siloxanes in particular cannot be prepared in this way.

Branched OH-rich siloxanes have long been a synthesis target with regard to environmentally friendly systems that condense with elimination of only water.

Access to branched, SiOH-rich siloxanes that are stable in water is described in EP0228978 through neutralization of alkali metal siliconates with carboxylic acids. Because of the high density of silanol groups, they are stable only in high aqueous dilution. Because of the absence of trimethylsilyl radicals, this process leads to the formation of a solid material.

By contrast, alkali metal siliconates react with large excesses of chlorosilanes to give SiOH-free or low-SiOH siloxanes. In this regard, the following publication is cited: Shchegolikhina, O. I. et al., Russian Chemical Bulletin, International Edition, Vol. 56, No. 1, pp. 83-90, January 2007 "cis_Tetra[(organo) (trimethylsiloxy)]cyclotetrasiloxanes: synthesis and mesomorphic properties."

Starting materials for cyclic, SiOH-free siloxanes are siliconate salts having an alkali metal:Si ratio of 1:1. They are converted to the corresponding siloxanes with a large excess (>8 equivalents based on siliconate) of trimethylchlorosilane in the presence of pyridine as a base, in high dilution in hexane as a solvent.

SUMMARY OF THE INVENTION

The invention provides a process for preparing siloxanes which are liquid at 25° C. and 1 bar, have 2% to 12% by weight of silanol groups, and are of the general formula (1):

$$M_a D_b T_c Q_d M'_e D'_f T'_g \quad (1),$$

in which metal salts of silanols of the general formula (2) or condensation products thereof $$R_1 Si(OH)_{4-l-m}(O^- Z^{r-}{}_{1/r})_m \quad (2)$$

are reacted with silanes of the general formula (3):

$$R'_n SiX_{4-n} \quad (3)$$

in a ratio which is calculated by the following equation:

mol of organosiliconate of the general formula (2): mol of silane of the general formula (3)=$x*(4-n)/m$, where $x = 0.8$ to $1.2$,
where
M is a $(R_3 SiO_{1/2})$ unit,
D is a $(R_2 SiO_{2/2})$ unit,
T is a $(RSiO_{3/2})$ unit,
Q is a $(SiO_{4/2})$ unit,
M' is a $(R'_3 SiO_{1/2})$ unit,
D' is a $(R'_2 SiO_{2/2})$ unit,
T' is a $(R'SiO_{3/2})$ unit,
R is an organic radical bonded to silicon via carbon,
R' is hydrogen, an unsubstituted or substituted alkoxy radical, a hydrocarbyl radical which is unsubstituted or substituted by halogen atoms or epoxy, thiol, nitrile, (poly) ether, carboxyalkyl, alkoxy or silyl groups and has 1 to 20 carbon atoms,
and the following relations apply:
$a = 0$ to $0.2*(a+b+c+d+e+f+g)$,
$b = 0$ to $0.2*(a+b+c+d+e+f+g)$,
$c = 0.3$ to $0.9*(a+b+c+d+e+f+g)$,
$d = 0$ to $0.2*(a+b+c+d+e+f+g)$,
$e = 0.05$ to $0.6*(a+b+c+d+e+f+g)$,
$f = 0$ to $0.6*(a+b+c+d+e+f+g)$,
$g = 0$ to $0.1*(a+b+c+d+e+f+g)$, and $(a+b+c+d+e+f+g) = 1$
l has values of $0.8$ to $1.3$,
r has values of 1, 2, 3 or 4,
n has the values of 1, 2 or 3,
Z is a metal cation and
X denotes hydrolysable radicals which are selected from halogen radicals and carboxyalkyl radical.

DETAILED DESCRIPTION OF THE PREFERRED EMBODIMENTS

The metal salts of silanols of the general formula (2) are also referred to as siliconates.

The molar ratio used with preference of organosiliconate of the general formula (2) to silane of the general formula (3)=$x*(4-n)/m$, with $x = 0.8$ to $1.2$, means that roughly equimolar amounts of hydrolysable radicals X from the silanes of the general formula (3) are used per siliconate group $O^-$. r denotes the valency of the metal and r+ the number of positive charges of the metal cation.

It was surprising to obtain liquid storage-stable SiOH-rich branched siloxanes in high yields by direct reaction of a solid metal siliconate with silane of the general formula (3), without solvent or in an inert organic solvent in which the siliconate has only very low solubility, if any, and without auxiliary base. In the case of reaction of a silanol-rich solid alkali metal siliconate with a silane of the general formula (3), what would have been expected was no specific reaction of the silanolate groups, but instead also a high degree of reaction of the silanol groups to form hydrogen halide and hence polycondensation to give low-silanol siloxanes of high molecular weight. Moreover, a subsequent aqueous workup leads to salt-free siloxanes, and if desired to very substantially alkoxy-free siloxanes.

The R radical is preferably a monovalent Si—C-bonded hydrocarbyl radical which is unsubstituted or substituted by halogen atoms, $C_{1-6}$-alkyl or $C_{1-6}$-alkoxy or silanol groups and has 1 to 30 carbon atoms, in which one or more mutually non-adjacent —$CH_2$— units may be replaced by —O— or —S— groups. The R radical may be linear, branched, cyclic, aromatic, saturated or unsaturated. Particular preference is given to unsubstituted alkyl radicals, cycloalkyl radicals, alkylaryl radicals, arylalkyl radicals and phenyl radicals. The hydrocarbyl radical R preferably has 1 to 8 carbon atoms, particular preference being given to the methyl, ethyl, 3,3,3-trifluoropropyl, vinyl, n-hexyl, isooctyl (e.g. 2,4,4-trimethylpent-1-yl) and phenyl radicals, more particularly to the methyl radical and the isooctyl radical, especially the methyl radical.

Further examples of R radicals are: n-propyl, 2-propyl, chloromethyl, methoxymethyl, phenoxymethyl, 2-cyanoethyl, 3-cyanopropyl, 3-chloropropyl, 3-thiopropyl, prop-2-en-1-yl, prop-2-en-2-yl, 2-(trimethylsilyl)ethyl, n-butyl, n-but-2-yl, 2-methylprop-1-yl, t-butyl, n-pentyl, cyclopentyl, cyclohexyl, n-heptyl, n-octyl, 2-ethylhexyl, n-nonyl, n-decyl, n-undecyl, 10-undecenyl, n-dodecyl, isotridecyl, n-tetradecyl, n-hexadecyl, benzyl, p-chlorophenyl, p-iodophenyl, p-bromophenyl, p-fluorophenyl, p-vinylphenyl, p-trifluoromethylphenyl, p-allyloxyphenyl, p-methoxyphenyl, o-(phenyl)phenyl, m-(phenyl)phenyl, p-(phenyl)phenyl, 1-naphthyl, 2-naphthyl, 2-phenyleth-1-yl, 1-phenyleth-1-yl, 3-phenylprop-1-yl, 3-phenoxyprop-1-yl radical. Further examples of R are —$(CH_2O)_o$—$R^8$, —$(CH_2CH_2O)_p$—$R^9$ and $CH_2CH(CH_3)O)_q$—$R^{10}$ radicals where o, p and q have values of 1 to 10, especially 1, 2, 3. $R^8$, $R^9$ and $R^{10}$ are preferably an alkyl radical which is unsubstituted or substituted by halogen atoms and has 1 to 6 carbon atoms. Examples of $R^8$, $R^9$ and $R^{10}$ radicals are the methyl, ethyl, propyl, allyl and butyl radicals, particular preference being given to the methyl radical.

Z is preferably an alkali metal, an alkaline earth metal, aluminium, zinc, iron in its di- or trivalent form, and titanium or zirconium. More particularly, Z is lithium, sodium, potassium or caesium, preference being given to sodium and potassium and particular preference to potassium. m in the general formula (2) is a number from 0.1 to 3; m is preferably at least 0.1, more preferably at least 0.4, especially at least 0.5, and at most 3, preferably at most 1, especially at most 0.8. With regard to the yield and silanol content, the range of m between 0.3 and 0.7 is found to be optimal.

The siliconates of the general formula (2) are preferably prepared by the processes described in WO2012/022544, WO2012/159874, WO13075969, WO13174689, WO15140075, WO15176977, for example by spray-drying of a reaction product of one or more organotrialkoxysilanes and alkali metal hydroxide solution or an alkali metal methylsiliconate.

As well as trifunctional siloxy units, the siliconates of the general formula (2) may contain minor proportions of mono-, di- or tetrafunctional siloxy units. However, the total molar proportion thereof is below 20 mol %.

The alkoxy content in the siliconates of the general formula (2) is preferably below 5% by weight, more preferably below 1% by weight, so as to result in a minimum alkoxy content in the silanol-containing siloxane of the general formula (1).

The siliconates of the general formula (2) are preferably used in pulverulent form with mean particle sizes below 500 μm, more preferably below 100 μm. They may optionally contain separating agents in the customary concentrations.

It is also possible to use mixtures of different siliconates.

The hydrolysable X radicals in the silane of the general formula (3) are preferably independently a halogen radical, more preferably the chlorine radical, or a carboxyalkyl radical having preferably 2 to 10 carbon atoms, more preferably the acetoxy radical.

n in the general formula (3) is preferably 2 or 3, more preferably 3.

The R' radicals in the silane of the general formula (3) are preferably independently a monovalent, optionally substituted alkoxy radical, especially unsubstituted alkoxy radical having 1 to 4 carbon atoms, a monovalent hydrocarbyl radical which is unsubstituted or substituted by halogen atoms or epoxy, thiol, nitrile, (poly)ether (e.g. (poly)ethylene oxide, (poly)propylene oxide, (poly)butylene oxide), carboxyalkyl, alkoxy or silyl groups, and has 1 to 20 carbon atoms.

Preferably, the R' radical is a hydrocarbyl radical having 1 to 16 and especially 1 to 8 carbon atoms, particular preference being given to the methyl, ethyl, n-prop-1-yl, 3,3,3-trifluoroprop-1-yl, vinyl, n-hex-1-yl, n-oct-1-yl, isooctyl (e.g. 2,4,4-trimethylpent-1-yl), n-hexadec-1-yl and phenyl radical, very particularly to the methyl, ethyl, phenyl and vinyl radical, and especially the methyl radical.

Further examples of R' radicals are: 2-prop-1-yl, chloromethyl, methoxymethyl, 3-chloroprop-1-yl, 2-(trimethylsilyl)eth-1-yl, 2-(trimethoxysilyl)eth-1-yl, 2-(triethoxysilyl)eth-1-yl, 2-(dimethoxymethylsilyl)eth-1-yl, 2-(diethoxymethylsilyl)eth-1-yl, n-but-1-yl, 2-but-1-yl, 2-methylprop-1-yl, t-butyl, n-pent-1-yl, cyclopentyl, cyclohexyl, n-kept-1-yl, 2-ethylhex-1-yl, n-non-1-yl, n-dec-1-yl, n-undec-1-yl, 10-undecen-1-yl, n-dodec-1-yl, isotridec-1-yl, n-tetradec-1-yl, n-hexadec-1-yl, ethynyl, allyl, benzyl, p-chlorophenyl, o-(phenyl)phenyl, m-(phenyl)phenyl, p-(phenyl)phenyl, p-phenoxyphenyl, p-methoxyphenyl, 1-naphthyl, 2-naphthyl, 2-phenyleth-1-yl, 1-phenyleth-1-yl, 3-phenylprop-1-yl, acetoxymethyl, 3-acetoxyprop-1-yl, acryloyloxymethyl, methacryloyloxymethyl, 3-acryloyloxyprop-1-yl, 3-methacryloyloxyprop-1-yl, —$(CH_2)_3$—$(OCH_2CH_2)_6OMe$, —$CH_2$—$(OCH_2CH_2)_6OMe$, —$(OCH_2CH_2)_6OMe$, —$(OCH_2CH_2)_6OOC$—$CH=CH_2$, —$OCH_2CH_2$—$OOC$—$CH=CH_2$, —$OCH_2CH_2$—$OOC$—$C(CH_3)=CH_2$, 3-glycidoxyprop-1-yl, 3-thioprop-1-yl, 2-cyanoeth-1-yl, and 3-cyanoprop-1-yl.

Examples of silanes of the general formula (3) are $HSiMeCl_2$, $H_2SiCl_2$, $Me_2SiCl_2$, $MeCl_2SiCH_2$—Cl, $ViSiMeCl_2$, $PhSiMeCl_2$, $H_3SiCl$, $Me_3SiCl$, $HSiMe_2Cl$, $ViSiMe_2Cl$, $PhSiMe_2Cl$, allyl-$SiMe_2Cl$, n-hexadec-1-yl-$SiMe_2Cl$, isooct-1-yl-$SiMe_2Cl$, $F_3C$—$CH_2CH_2$—$SiMe_2Cl$, $Me_2ClSiCH_2$—Cl, $(EtO)_3SiCl$, $(MeO)_3SiCl$, $(EtO)_2SiMeCl$, $(MeO)_2SiMeCl$, $EtOSiMe_2Cl$, $MeOSiMe_2Cl$, $ClSiMe_2$-$(CH_2)_3$—$OOC$—$CH=CH_2$, $ClSiMe_2$-$(CH_2)_3$—$OOC$—$C(CH_3)=CH_2$, Cl—$SiMe_2$-$(CH_2)_2$—$OOC$—$CH=CH_2$, Cl—$SiMe_2$-$O(CH_2)_2$—$OOC$—$C(CH_3)=CH_2$, $ClSiMe_2$-$(CH_2)_3$—$(O$—$CH_2$—$CH_2)_6OMe$, $ClSiMe_2$-$(CH_2)_3$—$(O$—$CH_2$—$CH_2)_6OOC$—$CH=CH_2$, $ClSiMe_2$-O—$CH_2$—

CH$_2$OOCCH=CH$_2$, ClSiMe$_2$-O—CH$_2$—CH$_2$—OOCC(CH$_3$)=CH$_2$, AcOSiMe$_2$-CH$_2$—CH$_2$—CH$_2$—SH, AcOSiMe$_2$-CH$_2$—CH$_2$—CH$_2$—O—CH(O)CH$_2$, ClSiMe$_2$-CH$_2$—CH$_2$—CH$_2$—CN, ClSiMe$_2$-CH$_2$—CH$_2$—CN, Me$_2$Si(OAc)$_2$, and Me$_3$SiOAc.

Me is the methyl radical, Et is the ethyl radical, Ph is the phenyl radical, Vi is the vinyl radical, allyl is the 2-propen-1-yl radical, and Ac is the acetyl radical.

Particular preference is given to Me$_3$SiCl, HSiMe$_2$Cl, ViSiMe$_2$Cl, PhSiMe$_2$Cl, allyl-SiMe$_2$Cl, ViSiMeCl$_2$ and Me$_2$SiCl$_2$, especially Me$_3$SiCl, ViSiMe$_2$Cl and Me$_2$SiCl$_2$.

The chlorosilanes are prepared in the methylchlorosilane synthesis by the Müller-Rochow process, or can be prepared as conversion products by chemical reactions by known methods (e.g. hydrosilylation, nucleophilic substitution, free-radical substitution) and are usually commercially available.

It is also possible to use mixtures of various silanes of the general formula (3). It is also possible to react the siliconate of the general formula (2) successively first with a substoichiometric proportion of silane of the general formula (3) and then successively with a second silane of the general formula (3). This procedure may also comprise several successive reactions with different silanes of the general formula (3). In this way, siloxanes of the general formula (1) with different M', D' and T' units are also obtainable.

The compounds of the general formula (1) are obtained by the process according to the invention by reaction of the siliconates (2) with the silanes of the general formula (3). This can be effected by addition of the siliconate to the silane or, conversely, by addition of the silane to the siliconate. If what is desired is a maximum silanol content in the target product and a high yield, the amount of silane used in the reaction is as far as possible exactly sufficient for only the (OZ'$^{r+}_{1/r}$) units in the siliconate to react. Advantageously, the siliconate of the general formula (2) is initially charged and the silane (3) is metered in. As a result, a small amount of highly reactive silane comes into contact with an excess of siliconate, which enhances the selectivity of the reaction—i.e. the reaction of Si—X from the silane with Si—(O$^-$Z'$^{r+}_{1/r}$) from the siliconate. At least one component here is advantageously in liquid or dissolved form. Most silanes of the general formula (3) are liquid at 25° C. under 1 bar; the siliconates of the general formula (2) are solid. One option is therefore to initially charge the siliconates in dry form in fine pulverulent distribution—for example in a fluidized bed produced by blowing in inert gas—or to dissolve or suspend it in an inert solvent, and to meter in the liquid silanes in neat form, in order to assure a very rapid reaction because of the good mixing. Preferably, the reaction takes place in a solvent. Solvents used are preferably aprotic polar and nonpolar organic solvents, preferably hydrocarbons, ethers, ketones and carboxylic esters, for example linear, branched or cyclic alkanes such as n-pentane, n-hexane, n-heptane, n-octane, isohexane, isooctane, cyclohexane, aromatics such as benzene, toluene, o-xylene, m-xylene, p-xylene, ethers such as diethyl ether, methyl ethyl ether, di-n-propyl ether, di-n-butyl ether, methyl t-butyl ether, diphenyl ether, methyl phenyl ether, tetrahydro-furan, methyl isobutyl ketone, acetone, methyl acetate, ethyl acetate, n-butyl acetate, methyl ethyl ketone (2-butanone), dioxane, tetrahydropyran, 4-methyltetrahydropyran, ethylene glycol methyl ether, diethylene glycol dimethyl ether, triethylene glycol dimethyl ether, ethylene glycol dibutyl ether or siloxanes, such as hexamethyldisiloxane, octamethyl-trisiloxane, octamethyl-cyclotetrasiloxane, decamethylcyclo-pentasiloxane, methyltris(trimethylsiloxy)silane or mixtures of various solvents.

The rate of the generally exothermic inventive reaction of siliconate of the general formula (2) and silane of the general formula (3) is preferably controlled via choice of the rate of metered addition of one component and choice of the temperature control of the reaction mixture. In the choice of the (maximum) reaction temperature for the reaction, the boiling points of the substances used and formed naturally play a crucial role, as do their thermal stabilities. Preferably, the reaction conditions are chosen so as not to exceed a temperature of 100° C., more preferably 80° C. and especially 40° C. in the reaction mixture. Lower temperatures possibly have the effect of a slight improvement in the selectivity, but lead to a longer reaction time and reduce the space-time yield; therefore, the lower limits for the reaction temperatures are preferably above −40° C., more preferably above −20° C., and especially above 0° C. It is possible here for the reaction mixture to be either cooled or heated, and for individual components to be brought to a particular temperature before they come into contact, for example in order to be able to exploit the heat of reaction. The process can be conducted either batchwise, for example in a stirred system, or continuously, for example in a loop reactor or tubular reactor, or, especially if an inert solvent is being dispensed with, in an extruder, a fluidized bed reactor or a paddle dryer.

Because of the hydrolysis sensitivity of the silanes of the general formula (3), the reaction of the siliconate of the general formula (2) with silane of the general formula (3) is preferably effected with exclusion of moisture, i.e. in a dried atmosphere or under reduced pressure, more preferably under inert gas, such as nitrogen, CO$_2$, argon, lean air, at standard pressure. Lower pressures may be advantageous when volatile by-products, for example HX, are to be removed immediately from the reaction mixture, in order to avoid unwanted side reactions (e.g. condensation).

The concentration of inert solvent used is preferably at least 40, more preferably at least 50 and especially at least 80 percent by weight based on siliconate of the general formula (2). As apparent in the examples, a higher level of dilution brings about a higher silanol content in the target product, but simultaneously reduces the space-time yield. The optimum for the particular reaction can be determined by the person skilled in the art in simple preliminary experiments.

The molar ratio of siliconate of the general formula (2) and silane of the general formula (3) naturally has an influence on the silanol content and yield of the target product.

The content of silanol groups in the siloxanes of the general formula (1) comes predominantly from the silanol groups of the metal salts of silanols of the general formula (2), and likewise any alkoxy radicals present in the siloxane of the general formula (1). The content thereof can be reduced by aqueous workup in the process according to the invention. A great advantage of the siloxanes of the general formula (1) prepared in accordance with the invention lies in the low alkoxy content which is preferably not more than 0.2 percent by weight, more preferably not more than 0.1 percent by weight, based on the siloxane of the general formula (1).

The molar ratio of organosiliconate of the general formula (2) to silane of the general formula (3)=x*(4−n)/m. In this ratio, x is preferably 1.0, but more preferably at least 0.9, especially 0.95, and more preferably not more than 1.1, especially 1.05.

Greater excesses of silane-bonded X mean that there is reaction not only of the metal ions bonded within the siliconate but also of free silanol groups in the siliconate, and hence release of HX. In the absence of an auxiliary base, this can set off condensation, which leads to a reduction in the silanol content in the target product of the general formula (1) and possibly an unwanted increase in molar mass. Significantly substoichiometric proportions, by contrast, leave unconverted SiOZ components in the siliconate, which can lead to a loss of yield of liquid siloxane of the general formula (1) and a rise in insoluble constituents.

Any by-product HX formed in the reaction of silane of the general formula (3) with protic hydrogen (for example from moisture in the starting materials or silanol groups in the siliconate) can be scavenged by adding an auxiliary base or a buffer system. Auxiliary bases used may be basic salts or nitrogen compounds such as amines, ureas, imines, guanidines, and amides. Examples of basic salts are ammonium hydrogencarbonate, sodium carbonate, sodium hydrogencarbonate, potassium carbonate, potassium hydrogencarbonate, calcium carbonate, calcium hydrogencarbonate, calcium oxide, magnesium carbonate, and magnesium oxide. Examples of nitrogen compounds are ammonia, ethylamine, butylamine, trimethylamine, triethylamine, tributylamine, urea, tetramethylurea, guanidine, tetramethylguanidine, imidazole, N-methylimidazole, N-ethylimidazole, piperidine, pyridine, and picoline. Preference is given to using nitrogen compounds in which the nitrogen atoms do not bear any hydrogen. Buffers used may, for example, be phosphate buffer or citrate buffer systems or amino acids. Preferably, the auxiliary base or buffer system is used at most in an equimolar amount relative to the silane of the general formula (3). For each molar equivalent X of the silane(s) of the general formula (3) used in the reaction mixture, preferably not more than 0.5, more preferably not more than 0.1 and especially 0.0 base equivalent of auxiliary base or buffer is used. It is also possible to use greater added amounts of auxiliary base or buffer, but these usually do not bring any advantage and instead reduce the space-time yield and hence the economic viability of the process. Preferably, the auxiliary base or buffer system is initially charged together with the siliconate of the general formula (2) and the silane of the general formula (3) is metered in. Alternatively, it is possible to meter both reactants in parallel into an initial charge of the auxiliary base or buffer system. It is also possible to use mixtures of different auxiliary bases and/or buffer systems.

Salts that are formed or any salts that are added in the reaction of siliconate of the general formula (2) with silane of the general formula (3) are either removed in solid form by filtration, centrifugation or sedimentation, or more preferably dissolved by addition of water and separated by means of phase separation from the target product or the solution of the target product in the organic solvent. In this case, the solubility of the inert solvent or solvent mixture chosen in water should be at a minimum and preferably should not exceed 10 percent by weight, more preferably 5 percent by weight at 20° C. This facilitates reprocessing for reuse of the solvent.

The amount of water added is such that the amount of salt and any auxiliary base added can be very substantially dissolved and that phase separation between the aqueous and organic phases is possible. It is preferably at least equal to and more preferably at least 3 times, especially at least 5 times, the amount of siliconate used.

It is optionally possible to facilitate phase separation in the aqueous workup if previously undissolved constituents are removed by filtration, centrifugation or sedimentation.

The siloxane of the general formula (1) is preferably isolated as a distillation residue by drawing off the volatile constituents (for example solvents or other volatile secondary constituents) by heating, for example over a short path in a batchwise distillation apparatus or a falling-film or thin-film evaporator, preferably under a reduced pressure of not more than 100 hPa, more preferably not more than 20 hPa, especially not more than 10 hPa. Preference is given to not exceeding 50° C. in order to avoid condensation of the silanol groups.

For the aqueous workup, the phase separation can be improved by adding an additional solvent having minimum solubility in water which preferably does not exceed 5% by weight at 20° C. It is also possible to use substances for improving phase separation in the aqueous workup, for example alcohols such as glycerol, methanol, ethanol, ethane-1,2-diol or propane-1,2-diol, or carboxylic esters such as methyl or ethyl acetate.

The crystallization of the siloxane of the general formula (1) is another means of isolation or purification.

The siloxane of the general formula (1) likewise forms part of the subject-matter of the invention.

Preference is given to preparing siloxanes in which $a=0$ to $0.15*(a+b+c+d+e+f+g)$.

Preference is given to preparing siloxanes in which $b=0$ to $0.15*(a+b+c+d+e+f+g)$.

Preference is given to preparing siloxanes in which $c=0.4$ to $0.85*(a+b+c+d+e+f+g)$, especially $c=0.5$ to $0.8*(a+b+c+d+e+f+g)$.

Preference is given to preparing siloxanes in which $d=0$ to $0.15*(a+b+c+d+e+f+g)$.

Preference is given to preparing siloxanes in which $e=0.1$ to $0.5*(a+b+c+d+e+f+g)$, especially $e=0.2$ to $0.45*(a+b+c+d+e+f+g)$.

Preference is given to preparing siloxanes in which $f=0$ to $0.5*(a+b+c+d+e+f+g)$, especially $f=0$ to $0.3*(a+b+c+d+e+f+g)$.

Preference is given to preparing siloxanes in which $g=0$ to $0.05*(a+b+c+d+e+f+g)$.

Preferred mean molar masses Mw of the siloxanes are between 400 and 6000 g/mol, especially between 500 and 4000 g/mol.

In the present application, all mean molar masses Mw are determined by means of GPC (column temperature 45° C., flow rate 1.00 ml/min, pressure 50.3 bar, calibrated against polystyrene standard; toluene as eluent; RI detector).

Preferably, the siloxanes of the general formula (1) have 3% to 10% by weight of silanol groups.

The silanol content of the siloxanes can be determined via the Zerevitinov reaction and NMR spectroscopy.

The siloxanes according to the invention can be used for applications where release of organic cleavage products is unwanted.

All the above symbols in the above formulae are each defined independently of one another. In all the formulae, the silicon atom is tetravalent.

In the examples and comparative examples which follow, unless stated otherwise in each case, all figures for amounts and percentages are based on weight and all reactions are conducted at a pressure of 1000 hPa (abs.).

The solids content in each case is determined with the HR73 Halogen Moisture Analyzer solids content balance from Mettler Toledo at 160° C.

EXAMPLES a) Preparation of Siliconate Powder

The siliconate powders used can be prepared according to WO2012/022544 (PCT/EP2011/061766) and WO2012/159874 (PCT/EP2012/058370) from methyltrimethoxysilane (WACKER CHEMIE AG) or mixtures of methyltrimethoxysilane with n-hexyltri-methoxysilane (Sigma-Aldrich) or isooctyltrimethoxysilane (SILRES® BS 1316, WACKER CHEMIE AG) and different proportions of KOH or NaOH and water. The solids content in each case is at least 95%. The composition can be determined by means of elemental analysis or from the mass balance in the preparation. In the case of the mixed methyl/hexyl and methyl/isooctyl systems and in the case of the spray-dried siliconates, a mean formula is determined from the stoichiometry of the starting materials (e.g. isooctyl:methyl:K=0.25:0.75:0.75=>mean formula of the siliconate: MeSi(OH)(OK)—[O—SiMe(OK)]$_2$—[OSi$^i$octyl(OH)$_2$]).

b) Reaction with Chlorosilane

One molar equivalent of Si-bonded chlorine in the form of chlorosilane or chlorosilane mixtures, based on one molar equivalent of alkali metal, in each case is metered cautiously into a suspension of siliconate powder in the particular solvent at 20° C. while stirring, in such a way that the temperature of the reaction mixture does not exceed 35° C. The mixture is left to come to room temperature and stirred for a period of time at room temperature, then the suspension is admixed with demineralized water, insoluble constituents are filtered off and, after phase separation, the upper organic phase is concentrated at 40° C./3 hPa. What remains as the residue in each case, is a clear colourless liquid, the composition of which is determined by means of $^1$H and $^{29}$Si NMR spectroscopy. In the $^{29}$Si NMR spectrum, it is possible to very accurately determine the stoichiometry of the siloxy units and hence the SiOH content; the $^1$H NMR spectrum provides clarification as to possible secondary constituents, especially residues of alkoxy groups and traces of solvent; it is also possible to verify the SiOH content determined in the $^{29}$Si NMR spectrum by derivatization of the SiOH groups with trichloroacetyl isocyanate. If required, the compounds obtained can additionally be characterized, for example, by size exclusion chromatography (SEC: mean molar mass and molar mass distribution), viscosity measurement, IR spectroscopy and chlorine content determination.

In the examples adduced hereinafter, the methoxy contents in the siloxanols according to the invention are below 0.01% by weight in each case (determined from the $^1$H and $^{29}$Si NMR spectra).

Abbreviations:
MTBE: methyl tert-butyl ether (abcr GmbH)
EtAc: ethyl acetate (Merck KGaA)
BuAc: n-butyl acetate (Merck KGaA)
MIBK: methyl isobutyl ketone (4-methylpentan-2-one) (Merck KGaA)
MEK: methyl ethyl ketone (butan-2-one) (Merck KGaA)
M: molar proportion of [Me$_3$SiO$_{1/2}$] from $^{29}$Si NMR (peaks between +12.5 ppm and +5.5 ppm)
T$^{(OH)2}$: molar proportion of [MeSi(OH)$_2$O$_{1/2}$] from $^{29}$Si NMR (peaks between −44 ppm and −46 ppm).
T$^{OH}$: molar proportion of [MeSi(OH)O$_{2/2}$] from $^{29}$Si NMR (peaks between −50 ppm and −60 ppm).
T: molar proportion of [MeSiO$_{3/2}$] from $^{29}$Si NMR (peaks between −62 ppm and −70 ppm).
D: molar proportion of [Me$_2$SiO$_{2/2}$] from $^{29}$Si NMR (peaks between −13 ppm and −24 ppm).

OH content: the proportion by weight of OH (molar mass 17 g/mol) in the siloxane (calculated from the $^{29}$Si NMR spectrum). In the case of the mixed siloxanes (methyl/ioctyl and methyl/n-hexyl), the mixing ratio of the alkyl radicals is taken into account in the calculation.

Yields: calculated on the basis of the mean formula of the siliconate used, assuming that potassium/sodium is replaced by Me$_3$Si or, in a corresponding mixture, by Me$_2$Si.

M/T/D yields: calculated on the basis of the composition found in the $^{29}$Si NMR spectrum and the molar amounts of siliconate and chlorosilane(s) used.

Example series 1: shows the relations between alkali metal/Si ratio and the type of alkali metal in the siliconate with respect to the SiOH content.

By the process described above, potassium methylsiliconate powder or sodium methylsiliconate powder is reacted with the equimolar amount of trimethylchlorosilane, based on alkali metal, in MTBE.

TABLE 1

| | Example | | | | |
|---|---|---|---|---|---|
| | 1.1 | 1.2 | 1.3 | 1.4 | 1.5 |
| Alkali metal | K | K | K | Na | K |
| Molar alkali metal:Si ratio | 0.3 | 0.56 | 0.85 | 0.85 | 1.2 |
| Solvent | MTBE | MTBE | MTBE | MTBE | MTBE |
| Siliconate concentration [% by wt.] | 8.6 | 8.3 | 8.6 | 8.6 | 8.6 |
| M | 30 | 31.7 | 46.4 | 26.2 | 54.1 |
| T$^{OH}$ | 23 | 33.1 | 18.7 | 39.9 | 10.1 |
| T$^{(OH)2}$ | 0 | 0.6 | 0.9 | 2 | 0.3 |
| T | 47 | 34.6 | 34.0 | 31.9 | 35.4 |
| OH content (% by wt.) | 5.3 | 7.8 | 4.6 | 10 | 2.4 |
| Filtercake in % by weight based on siliconate | 47.3 | 6.7 | 3.3 | 86.2 | 13.3 |
| M/T yields [%] | 64/43 | 84/95 | 88/100 | 11/26 | 70/77 |
| Yield [%] | 48 | 88 | 92 | 19 | 74 |

Comparing batches 1.1, 1.2, 1.3 and 1.5, it is noticeable that there is a drop in the silanol concentration with rising potassium content. It is apparent from 1.3 and 1.4 that sodium in the siliconate does lead to higher silanol contents, but there is a huge rise in the solids content.

Example series 2 shows the influence of the type of solvent. It becomes clear from this that the solvent has a significant effect on the SiOH content. The highest SiOH concentrations can be achieved with MTBE and ethyl acetate, whereas butyl acetate and MIBK give somewhat higher yields. MEK and MIBK have the drawback of discolouration, which is attributable to the reactivity of the two ketones with bases.

Feedstocks/amounts used:
15 g of potassium methylsiliconate K:Si=0.56 [in tetrameric form according to elemental analysis: 0.147 mol MeSi, 0.08 mol K]
8.6 g of trimethylchlorosilane (0.08 mol)
165 g of solvent
105 g of demineralized water (for workup)

TABLE 2

| | Example | | | | | |
|---|---|---|---|---|---|---|
| | 2.0 | 2.1 | 2.2 | 2.3 | 2.4 | 2.5 |
| Solvent | Isopar® E | MTBE | EtAc | BuAc | MIBK | MEK |
| M | 34.2 | 31.7 | 30.5 | 33.0 | 33.5 | 33.4 |
| T$^{OH}$ | 9.2 | 33.1 | 28.9 | 25.8 | 22.6 | 21.4 |
| T$^{(OH)2}$ | 0 | 0.6 | 0.4 | 0.2 | 0.4 | 0.6 |
| T | 56.6 | 34.6 | 40.3 | 41.0 | 43.4 | 44.7 |

TABLE 2-continued

| | Example | | | | | |
|---|---|---|---|---|---|---|
| | 2.0 | 2.1 | 2.2 | 2.3 | 2.4 | 2.5 |
| OH content (% by wt.) | 2.1 | 7.8 | 6.8 | 6.0 | 5.4 | 5.2 |
| Final weight [g] | 7.2 | 15.5 | 15.8 | 16.3 | 17.3 | 16.3 |
| Filtercake [g] | 8.1 | 1 | 0.8 | 0.6 | 1 | 0.7 |
| Based on siliconate | 54% | 6.7% | 5.3% | 4% | 6.7% | 4.7% |
| M/T yields [%] | 45/44 | 84/95 | 82/99 | 92/98 | 100/100 | 93/98 |
| Yield [%] | 41 | 88 | 90 | 93 | 99 | 93 |
| Appearance | colourless/cloudy | colourless/clear | colourless/clear | colourless/clear | yellowish/clear | brown/clear |

Example series 3 shows the influences of solvent concentration and postreaction time in the case of MTBE A higher solvent content and/or shorter reaction times give rise to a higher silanol content, with a rise in the proportion of solids (resins of relatively high molecular weight, methylsilicic acids) in the latter case at the expense of yield (3.2a/b).

Feedstocks/amounts used:

15 g of potassium methylsiliconate K:Si=0.56 [in tetrameric form according to elemental analysis: 0.147 mol MeSi, 0.08 mol K]

8.6 g of trimethylchlorosilane (0.08 mol), MTBE. The amount of water for the workup in each case is such that good phase separation is possible.

TABLE 3

| | Example | | | |
|---|---|---|---|---|
| | 3.1 | 3.2a | 3.2b | 3.3 |
| Concentration of siliconate [% by wt.] | 8.3 | 16.7 | 16.7 | 23 |
| Postreaction time at 20° C. | 20 h | 20 h | 1.5 h | 70 h |
| M | 31.7 | 33.5 | 31.7 | 32.3 |
| Mw (g/mol) | n.d. | 600 | n.d. | 1400 |
| $T^{OH}$ | 33.1 | 27.0 | 29.2 | 15.6 |
| $T^{(OH)2}$ | 0.6 | 0.4 | 0.6 | 0 |

TABLE 3-continued

| | Example | | | |
|---|---|---|---|---|
| | 3.1 | 3.2a | 3.2b | 3.3 |
| T | 34.6 | 39.1 | 38.5 | 52.1 |
| OH content (% by wt.) | 7.8 | 6.4 | 7.0 | 3.6 |
| Final weight [g] | 15.5 | 15.6 | 14.0 | 14.1 |
| Filtercake [g] | 1 | 1.6 | 3.2 | 2.6 |
| Based on siliconate | 6.7% | 10.7% | 21.3% | 17.3% |
| M/T yields [%] | 84/95 | 89/93 | 76/86 | 79/87 |
| Yield [%] | 88 | 89 | 80 | 80 |

Example series 4 shows the influence of relatively long alkyl radicals in the siliconate TABLE 4a n-hexyl/methylsiloxanes

| | Example | | |
|---|---|---|---|
| | 4a.1 | 4a.2 | 4a.3 |
| Molar ratios | n-hexyl:Me:K 25:75:75 azeotropic drying | n-hexyl:Me:K 17:83:83 spray drying | n-hexyl:Me:K 17:83:83 azeotropic drying |
| Amount used [g] | 15 | 6.7 | 15 |
| Solvent | MTBE | MTBE | MTBE |
| Siliconate concentration [% by wt.] | 8.6% | 8.7% | 8.6% |
| M | 43.5 | 40.6 | 40.9 |
| $T^{OH}$ | 14.4 | 20.9 | 15.7 |
| $T^{(OH)2}$ | 1.0 | 1.3 | 0.9 |
| T | 41.2 | 37.1 | 42.5 |
| OH content (% by wt.) | 3.3 | 4.9 | 3.7 |
| Final weight [g] | 15 | 7 | 13.5 |
| Filtercake [g] | 0.8 | 0 | 2.2 |
| Based on siliconate | 5.3% | 0% | 14.7% |
| Yield | 84% | 85% | 73% |

The spray-dried siliconate gives higher yields and a distinctly higher silanol content (4a.2/3). A higher hexyl content in the siliconate results in a better yield with comparable silanol content (4a.1/3).

TABLE 4b $^i$octyl/methylsiloxanes

| | Example | | | | |
|---|---|---|---|---|---|
| | 4b.1 | 4b.2 | 4b.3 | 4b.4 | 4b.5 |
| Molar ratios | $^i$octyl:Me:K 17:83:83 azeotropic drying | $^i$octyl:Me:K 17:83:83 spray-drying | $^i$octyl:Me:K 25:75:75 azeotropic drying | $^i$octyl:Me:K 25:75:75 spray-drying | $^i$octyl:Me:K 25:75:75 spray-drying |
| Amount used [g] | 15 | 7.2 | 15 | 15 | 15 |
| Solvent | MTBE | MTBE | MTBE | MTBE | Isopar E |
| Siliconate concentration [% by wt.] | 8.6% | 6.7% | 8.6% | 8.6% | 8.6% |
| M | 42.0 | 37.3 | 39.5 | 24.8 | 19.9 |
| $T^{OH}$ | 14.5 | 24.1 | 23.9 | 13.2 | 21.1 |
| $T^{(OH)2}$ | 0.6 | 2.4 | 1.8 | 0 | 0 |
| T | 42.9 | 36.2 | 34.9 | 62.1 | 59 |
| OH content (% by wt.) | 3.2 | 5.8 | 5.2 | 2.5 | 3.9 |
| Final weight [g] | 13.8 | 6.7 | 14 | 12.4 | 11.8 |
| Filtercake [g] | 1 | 0.6 | 1.3 | 0 | 1.2 |

TABLE 4b-continued

| | *i*octyl/methylsiloxanes | | | | |
|---|---|---|---|---|---|
| | Example | | | | |
| | 4b.1 | 4b.2 | 4b.3 | 4b.4 | 4b.5 |
| Based on siliconate | 6.7% | 8.3% | 8.7% | 0% | 8% |
| Yield | 75% | 76% | 78% | 69% | 66% |

It is clear that spray-dried powder gives a much higher silanol concentration than that subjected to azeotropic drying (4b.1/2). This can be attributed to condensation effects during drying. In the case of a relatively low potassium content, the effect is apparently reversed (4b.3/4). However, an increase in the silanol content can then be achieved with a nonpolar solvent (4b.5).

Example series 5 shows the results with mixtures of trimethylchlorosilane and dimethyldichlorosilane with a potassium methylsiliconate (K:Si=0.5) 16.7% by weight in MTBE[1])

TABLE 5

| | Example | |
|---|---|---|
| | 5.1 | 5.2 |
| Molar K:M3:M2 ratio | 1:0.8:0.1 | 1:0.6:0.2 |
| M | 27.2 | 21.4 |
| $T^{OH}$ | 24.5 | 17.8 |
| $T^{(OH)2}$ | 0.3 | 0.2 |
| T | 44.4 | 53.4 |
| D | 3.5 | 7.2 |
| $D^{OH}$ | 0.2 | 0.5 |
| OH content (% by wt.) | 5.9 | 4.4 |
| Final weight [g] | 14.7 | 8.6 |
| Filtercake [g] | 2.2 | 6.3 |
| Based on siliconate | 14.7% | 42% |
| M/D/T yields [%] | 86/94/92 | 54/57/56 |
| Yield [%] | 84 | 50 |
| Methoxy content [% by wt.] | 0.009 | n.d. |

It is apparent from this that, with increasing proportion of difunctional units (dimethyldichlorosilane), there is a drop in the yield of liquid siloxane and in the silanol content.

Example 6

Reaction of siliconate with lactic acid (noninventive, analogous to EP0228978)

Into a suspension of 15 g of potassium methylsiliconate K:Si=0.56 [in tetrameric form according to elemental analysis: 0.147 mol MeSi, 0.08 mol K] (K:Si=0.56; 0.08 mol K) in 75 g of MTBE is metered a solution of 8.7 g of 85% lactic acid in 17.9 g of water at 20.5° C. while stirring within 10 minutes. In the course of this, the temperature of the reaction mixture rises to 22.7° C. The cloudy mixture is left to stir at room temperature for 24 hours and then suspended particles are filtered off. The filtrate separates into a two colourless, clear phases. The upper phase is removed and concentrated at 40° C./3 hPa. The residue that remains is 15.6 g of a colourless solid which, according to the $^{29}$Si NMR spectrum, has the following composition: 19.9 mol % of [MeSi(OH)O$_{2/2}$] and 80.1% of [MeSiO$_{3/2}$]; the calculated OH content is 4.9% by weight.

Because of the absence of trimethylsilyl radicals, this process leads to the formation of a solid.

The invention claimed is:

1. A process for preparing siloxanes which are liquid at 25° C. and 1 bar, have 2% to 12% by weight of silanol groups, and are of the formula (1):

$$M_a D_b T_c Q_d M'_e D'_f T'_g \quad (1),$$

comprising reacting metal salts of silanols of the formula (2):

or condensation products thereof, with silanes of the formula (3):

$$R'_n SiX_{4-n} \quad (3)$$

in a ratio which is calculated by the following equation:

mol of organosiliconate of the formula (2): mol of silane of the formula (3)=$x*(4-n)/m$, where x=0.95 to 1.05,
M is a (R$_3$SiO$_{1/2}$) unit,
D is a (R$_2$SiO$_{2/2}$) unit,
T is a (RSiO$_{3/2}$) unit,
Q is a (SiO$_{4/2}$) unit,
M' is a (R'$_3$SiO$_{1/2}$) unit,
D' is a (R'$_2$SiO$_{2/2}$) unit,
T' is a (R'SiO$_{3/2}$) unit,
R is an organic radical bonded to silicon via carbon,
R' is hydrogen, an unsubstituted or substituted alkoxy radical, or a hydrocarbyl radical which is unsubstituted or substituted by halogen atoms or epoxy, thiol, nitrile, (poly)ether, carboxyalkyl, alkoxy or silyl groups and has 1 to 20 carbon atoms,
and the following relations apply:
a=0 to 0.2*(a+b+c+d+e+f+g),
b=0 to 0.2*(a+b+c+d+e+f+g),
c=0.3 to 0.9*(a+b+c+d+e+f+g),
d=0 to 0.2*(a+b+c+d+e+f+g),
e=0.05 to 0.6*(a+b+c+d+e+f+g),
f=0 to 0.6*(a+b+c+d+e+f+g),
g=0 to 0.1*(a+b+c+d+e+f+g),
and (a+b+c+d+e+f+g)=1
l has values of 0.8 to 1.3,
m is 0.3 to 0.7,
r has values of 1, 2, 3 or 4,
n has values of 1, 2 or 3,
Z is a metal cation, and
X denotes hydrolysable radicals which are selected from halogen radicals and carboxyalkyl radicals.

2. The process of claim 1, wherein R is a hydrocarbyl radical having 1 to 8 carbon atoms.

3. The process of claim 1, in which R' is a hydrocarbyl radical having 1 to 8 carbon atoms.

4. The process of claim 1, wherein Z is an alkali metal, alkaline earth metal, aluminium, zinc, or iron.

5. The process of claim 1, wherein X is a halogen radical or a carboxyalkyl radical having 2 to 10 carbon atoms.

6. The process of claim 1, wherein the reaction is conducted in a solvent comprising an aprotic polar or nonpolar organic solvent.

7. A siloxane which is liquid at 25° C. and 1 bar, contains from 2 to 12 weight percent of silanol groups, and has the formula (1) of claim 1.

8. The siloxane of claim 7, wherein R is a hydrocarbyl radical having 1 to 8 carbon atoms.

9. The siloxane of claim 7, wherein R' is a hydrocarbyl radical having 1 to 8 carbon atoms.

10. The siloxane of claim 7, wherein the alkoxy content of the siloxane is not more than 0.2 percent by weight.

* * * * *